United States Patent [19]
Derrieu et al.

[11] Patent Number: 5,935,603
[45] Date of Patent: Aug. 10, 1999

[54] WATER SOLUBLE POWDER FORM COMPOSITIONS AND THEIR APPLICATIONS THEREOF

[75] Inventors: Guy Derrieu, Cagnes-sur-Mer; Jean-Luc Pougnas, Saint Laurent du Var; Olivier Broussaud, Nice, all of France

[73] Assignee: Virbac SA, Carros, France

[21] Appl. No.: 08/945,246

[22] PCT Filed: Apr. 25, 1996

[86] PCT No.: PCT/FR96/00635

§ 371 Date: Dec. 22, 1997

§ 102(e) Date: Dec. 22, 1997

[87] PCT Pub. No.: WO96/33743

PCT Pub. Date: Oct. 31, 1996

[30] Foreign Application Priority Data

Apr. 26, 1995 [FR] France .................................. 95 04980

[51] Int. Cl.$^6$ ............................ A61K 9/14; A61K 31/43; A61K 31/545; A61K 31/47
[52] U.S. Cl. ........................ 424/489; 514/199; 514/200; 514/311; 514/600; 514/951
[58] Field of Search ............................ 424/489; 514/199, 514/200, 311, 600, 951

[56] References Cited

U.S. PATENT DOCUMENTS

| | | | |
|---|---|---|---|
| 4,726,951 | 2/1988 | Panoz et al. ............................. | 424/465 |
| 4,933,334 | 6/1990 | Shimizu et al. ......................... | 514/202 |
| 5,595,762 | 1/1997 | Derrieu et al. .......................... | 424/490 |

FOREIGN PATENT DOCUMENTS

| | | |
|---|---|---|
| 319856 | 6/1989 | European Pat. Off. . |
| 415567 | 3/1991 | European Pat. Off. . |

*Primary Examiner*—Kevin E. Weddington
*Attorney, Agent, or Firm*—Alston & Bird LLP

[57] ABSTRACT

Water soluble, powder form compositions suitable for completely and rapidly dissolving active ingredients which usually only dissolve in water in the presence of base salts, such as antibiotics of the betalactamide family, for example penicillins and their derivatives, cephalosporins and their derivatives, or other active ingredients such as sulphamides and quinolones, for oral absorption thereof and their applications. The water soluble powder form compositions contain, in combination and in powder form, at least one water soluble active ingredient, not in salt form, and with an exclusively alkaline pH, an excess of one or more strong base salts, and one or more buffers comprising one or more substances and capable of maintaining the pH of the medium at a level below the normal solubilization pH of said active ingredient. Aqueous solution compositions obtained from said powder form compositions are also described.

10 Claims, No Drawings

WATER SOLUBLE POWDER FORM COMPOSITIONS AND THEIR APPLICATIONS THEREOF

The present invention relates to pulverulent and water-soluble compositions which are suitable for completely and rapidly dissolving active ingredients which are normally only soluble in water in the presence of basic salts, such as antibiotics of the beta-lactamide family, such as penicillins or their derivatives, cephalosporins or their derivatives, or other active ingredients such as sulfamides and quinolones, so that they can be absorbed by the oral route. Such compositions enable the active ingredients to be dissolved very rapidly, whatever the nature of the water employed, and, at the same time, provide an aqueous solution of active ingredient which is stable for from one to several days, thereby enabling them to be stored and therefore used over a period of one or more days.

The abovementioned active ingredients are known to lead rapidly, following oral absorption, to high concentrations in the blood. Given their broad spectrum of activity against both Gram-positive bacteria and Gram-negative bacteria, they have many therapeutic indications in human pharmacy or in the veterinary field: calves, pigs, poultry and others.

Soluble derivatives of the penicillins, such as the sodium or potassium salts of penicillin G, or the sodium salt of amoxicillin, or else the sodium salt of cefalexin, exist and have been very amply described in the literature. While being very soluble, these compounds suffer from the major drawback of at the same time exhibiting:

instability in solution, due to the alkaline pH of the medium which they generate, and also instability while they are being stored in the powdered state.

Thus, they are generally obtained by salifying in aqueous, frequently hot, solution and then evaporating the water using a standard technique such as lyophilization or spray drying; these different operations set in train well known reactions which degrade these molecules in alkaline medium, as soon as they have been prepared, with the said degradation reactions continuing even when the said compounds are in the pulverulent state.

In order to obtain aqueous solutions which can be administered by the oral route, the soluble salts of the penicillins are, for example, employed directly or formed in situ using pharmaceutically acceptable inorganic (solubilizing) salts of sodium, potassium, magnesium, ammonium or substituted ammonium. In these two cases, if the solubility is acceptable, the active ingredient is observed to be destroyed rapidly due to the alkaline character of the solution. This degradation is more substantial in the case of mixtures of antibiotics and inorganic (solubilizing) salts since, in order to achieve the desired solubility, it is necessary to have an excess of the solubilizing agent; however, on the one hand, the inorganic salt has a very basic character and, on the other hand, the stoichiometric ratio of 1:1, which is required in order to obtain dissolution, has to be modified in order to obtain the best solubility possible, leading to a particularly high pH being obtained. Nevertheless, mixtures of antibiotics and inorganic salts are more stable in the pulverulent state than are the soluble salts of penicillins.

Consequently, the object of the present invention is to make available a pulverulent composition which makes it possible to achieve, at one and the same time:

rapid and total solubility in water, whatever the characteristics of the latter, stability in water for at least 24 hours, and stability in the pulverulent state for at least 2 years.

The present invention relates to pulverulent, water-soluble compositions which are characterized in that they comprise, in combination and in pulverulent form:

at least one non-salified active ingredient which is only soluble in water at alkaline pH, at least one salt of a strong base, which is present in excess, and at least one buffer which is formed from one or more substances which are suitable for maintaining the pH of the medium at a value which is lower than the normal pH for solubilizing the said active ingredient.

Unexpectedly, such pulverulent compositions, which comprise, in combination, a salt of a strong base, which is employed in excess, and a buffer, that is to say a substance, or, more precisely, a mixture of substances, which maintains the pH of the medium in a precise pH range during and after dissolution, make it possible to solubilize the active ingredient very rapidly while preserving its integrity in solution over a period of from one to several days. The quantities of salt of a strong base and of buffer depend on the quantity and the nature of the active molecule to be solubilized.

According to one advantageous embodiment of the said pulverulent composition, the salt of a strong base is advantageously selected from the group consisting of basic salts which comprise, as anion, carbonate, bicarbonate or sulphate ions and, as cation, sodium, potassium, ammonium or substituted ammonium ions. Sodium carbonate will be selected by preference.

According to another advantageous embodiment of the said pulverulent composition, the buffer is advantageously selected from the group which comprises phosphate buffers, leading to pH values of between 6.5 and 8.0, sodium chloride/disodium phosphate buffers, leading to pH values of between 6.8 and 7.5, sodium chloride/trisaminomethane buffers leading to a pH value of about 7.5, citro-phosphate buffers leading to pH values between 6.5 and 7.9, borate buffers in the neighbourhood of pH 7.5, and all the possible combinations for obtaining a buffer at the desired pH. Phosphate buffers will be selected by preference.

According to another advantageous embodiment of the said pulverulent composition, it additionally comprises at least one of the following compounds: chelating agents, anti-caking agents (water-fixing agents), flavours or perfumes or fillers, in the pulverulent state.

According to another embodiment of the said pulverulent composition, it contains between 1 and 60% (by weight based on the total pulverulent composition) of active ingredient.

The composition is produced and packaged, in a manner known to the skilled person, by mixing powder-form components in the dry and packing them in packages which are suitable for this type of formulation.

Water-soluble pulverulent compositions of this nature can be used, in particular, in treatments administered by the oral route, in particular in commercial animal husbandry. Their solubility and their stability in solution enable the medicament, for example in the veterinary field, to be dispensed in a homogeneous manner through the equipment for distributing drinking water, in particular the automated equipment used in commercial animal husbandry. Drinking water is a very good vector for ensuring that the medicaments are absorbed by the animals for the purposes of treatment or prevention. A therapeutic scheme can be followed precisely, can be adjusted according to need and can be continued for several days if required.

The posology for amoxicillin, for example, is 10 mg of active ingredient per kg of live weight and per day (mg.kg$^{-1}$.d$^{-1}$). Depending on the weight of the animal and its daily consumption of water, this results in having a concentration of active ingredient in the drinking water of between 50 and 200 mg per liter. The treatment should be carried out for from 3 to 5 days. This posology can be doubled for the first day in serious cases, that is to say between 100 and 400 mg per liter of water.

The present invention also relates to compositions in the form of aqueous solutions, which compositions are characterized in that they comprise a pulverulent composition according to the invention and water.

Concentrated solutions or dilute solutions of active ingredient are obtained depending on the quantity of water which is combined with the said pulverulent composition; while very concentrated solutions may only be stable for a few hours, dilute solutions, which contain efficacious doses of active ingredients, should be stable for at least 24 hours.

The fact that even concentrated solutions are stable for at least a few hours facilitates the preparation and use of the dilute solutions, which are those which are in fact dispensed.

As pointed out above, the solution of the medicament can be obtained directly by dissolving the necessary quantity of active ingredient in the requisite volume of water. This mode of operation is employed, in particular, for treating a few animals, that is to say when the volume of water is not too substantial, since it would otherwise be difficult to handle. This direct dissolution is also employed for large volumes in tanks which are equipped with a stirring device. This demonstrates the crucial importance of having very satisfactory and rapid dissolution.

In order to prepare larger volumes, which are distributed from tanks, it is easier to prepare a concentrated solution in a receptacle, such as a bucket, that is to say such that the necessary quantity of active ingredient is dispersed in a volume of water which is from 20 to 100 times smaller than the final volume. The concentrated solution is then transferred to the tank, which contains the remainder of the water which is required. Good dissolution, even when the solution is concentrated, makes it possible to pour an active ingredient which is in solution, and not in suspension, into the tank, thereby avoiding the problems associated with handling a suspension, namely sedimentation at the bottom of the tank, resulting in a large number of technical problems such as blockage of the distribution pipelines.

Unexpectedly, the solutions according to the invention, which have been prepared from pulverulent compositions as defined above, in fact make it possible to obtain:

a true solution, which is important for. homogeneity;
stability in solution, such that recrystallization is avoided;
no degradation of the active ingredient in solution, such that the treatment can be recommended for one day or more.

The present invention also relates to a process for preparing the said compositions in the form of aqueous solutions, which process is characterized in that it comprises:

(i) preparing a pulverulent composition according to the invention, and
(ii) solubilizing the said composition in a quantity of water which is sufficient for obtaining, in the final solution, a quantity of active ingredient per kg of animal to be treated which is effective for at least 24 hours.

Advantageously, as pointed out above, step (ii) can be carried out in two stages, namely preparation of a concentrated solution and dilution of the concentrated solution, so as to obtain, in the final solution, a quantity of active ingredient per kg of animal to be treated which is effective for at least 24 hours.

Such compositions, in the form of aqueous solutions, are stable for from 1 to several days.

Apart from the abovementioned provisions, the invention also includes other provisions, which will emerge from the following description, which refers to examples of the combination to which the present invention relates.

It should be understood, however, that these examples are given by way of illustrating the subject-matter of the invention, to which they in no way constitute a limitation.

EXAMPLE 1

Soluble Composition Containing 10 Percent Amoxicillin (Composition A)

1) Preparation of a pulverulent composition according to the invention:

Amoxicillin (in trihydrate form) (10 g, that is 27.4 mmol) is mixed mechanically with anhydrous sodium carbonate (3 g, that is 28.3 mmol), monosodium phosphate dihydrate (13 g), disodium phosphate (1 g) and anhydrous glucose, which is a soluble filler which enables the concentrations to be adjusted so as to obtain a composition containing 10% (w/w) of active ingredient (71.2 g) (=composition A).

2) Preparation of the aqueous solution:

40 g of composition A are dissolved in 1000 ml of tap water.

3) Study comparing the properties of the compositions according to the invention with those of compositions of the prior art:

a) Solubility test.

The speeds at which composition A, described above, and sodium amoxicillin dissolved were compared:

The same quantities of amoxicillin, that is:

(1) 40 g of composition A, equivalent to 4 g of amoxicillin (in trihydrate form), and
(2) 4 g of amoxicillin (in sodium form), were dissolved in 1000 ml of tap water; the time for dissolution and the pH of each of the solutions obtained were noted.

|     | Product | Time for dissolution | Final pH |
| --- | --- | --- | --- |
| (1) | Composition A (40 g) | 45 sec | 7.7 |
| (2) | Amoxicillin (Na) (4 g) | 42 sec | 8.7 |

The solubility of composition A is comparable to that of the sodium salt of amoxicillin, which is the most soluble form of this antibiotic. The fact should be noted that, even if the speeds of dissolution are equivalent, the pH values of the solutions obtained were different.

b) Role of each constituent of the composition: study of the appearance of the solution or suspension obtained, of its solubility and of its pH.

The same quantities of amoxicillin (in trihydrate form), that is 4 g, were added to solutions consisting of:

in the first case: sodium carbonate (3 g) and water (1000 ml);
in the second case: monosodium phosphate dihydrate (13 g), disodium phosphate (1 g) and water (1000 ml), and
in the third case: sodium carbonate (3 g), monosodium phosphate dihydrate (13 g), disodium phosphate (1 g) and water (1000 ml), equivalent to the salt of a strong base/buffer combination which is used in composition A. The appearance, the time for dissolution and the pH of each of the solutions obtained were noted.

| Solvent | Appearance of the solution | Time for dissolution | Final pH |
|---------|---------------------------|----------------------|----------|
| 1st solvent Na carbonate | Solution | 45 sec. | 8.5 |
| 2nd solvent buffer | Presence of insoluble material | Not determined | 6.5 |
| 3rd solvent Na carbonate and buffer | Solution | 45 sec. | 7.6 | c) Study comparing the stability of amoxicillin (in trihydrate form) which is employed in composition A, of amoxicillin (in trihydrate form) which is combined solely with a salt of a strong base, and of sodium amoxicillin.

c-1 "normally used solution" assay:

The same quantities of amoxicillin, that is:

(1) 0.8 g of composition A (that is 80 mg of amoxicillin (in trihydrate form)), (2) 80 mg of amoxicillin (in trihydrate form) combined with 24 mg of sodium carbonate, and (3) 80 mg of amoxicillin (in sodium form) were dissolved in 1000 ml of tap water (effective dose required for treating poultry).

| | Product | pH | $t_0$ | $t_4$ | $t_{12}$ | $t_{24}$ | $t_{36}$ |
|---|---------|-----|-------|-------|----------|----------|----------|
| (1) | Composition A (0.8 g) | 7.6 | 100.5 | 99.2 | 100.8 | 101.0 | 98.7 |
| (2) | Amoxicillin ($3H_2O$) (80 mg) Na carbonate (24 mg) | 9.2 | 100.1 | 87.8 | 66.2 | — | — |
| (3) | Amoxiciliin (Na) (80 mg) | 8.7 | 100.0 | 92.1 | 75.4 | — | — |

Content of amoxicillin in solution at time (in hours)

Composition A, to which the present invention relates, leads, in solution, to the amoxicillin being stable, over a period of more than 36 hours, when compared with sodium amoxicillin, on the one hand, and with amoxicillin trihydrate which is combined with an inorganic sodium salt (equivalent to the salt employed in composition A), on the other hand. Unexpectedly, solubilization at a non-alkaline pH does indeed improve stability significantly; consequently, the pH values are one of the keys to the instability or stability of the aqueous compositions which are obtained.

c-2 "concentrated solution" assay:

The same quantities of amoxicillin, that is:

(1) 40 g of composition A (that is 4 g of amoxicillin (in trihydrate form)), (2) 4 g of amoxicillin (in trihydrate form) combined with 1.2 g of sodium carbonate, and (3) 4 g of amoxicillin (in sodium form), were separately dissolved in 1000 ml of tap water (concentration employed in order to achieve a preliminary solubilization before diluting for use).

| | Product | pH | $t_0$ | $t_4$ | $t_{12}$ | $t_{24}$ |
|---|---------|-----|-------|-------|----------|----------|
| (1) | Composition A (40 g) | 7.7 | 100.2 | 99.2 | 98.3 | 97.1 |
| (2) | Amoxicillin ($3H_2O$) (4 g) Na carbonate (1.2 g) | 9.4 | 100.2 | 80.3 | — | — |
| (3) | Amoxicillin (Na) (4 g) | 8.7 | 100.0 | 87.2 | — | — |

Content of amoxicillin in solution in % at time (in hours)

In the same way as in the preceding paragraph (c-1), the stability of the amoxicillin in a composition according to the invention is found to be superior, in solution, to that of sodium amoxicillin and of amoxicillin trihydrate which is combined with sodium carbonate. In view of the high content of active ingredient in the concentrated solutions, the experiment records a shorter period of stability, i.e. 12 hours instead of the 36 hours for the composition A-based solution described in paragraph c-1. This time is ample for preparing solutions which are of therapeutic value and which are stable in solution for more than 24 hours.

d) Stability over time

The stabilities, at ambient temperature (25° C.), of composition A, of amoxicillin trihydrate, of a composition A', equivalent to composition A without the buffer, that is 10 g of amoxicillin (in trihydrate form) together with 3 g of anhydrous sodium carbonate and anhydrous glucose (85.2 g), and of sodium amoxicillin, which compounds and compositions were packaged in the sachets which are normally employed for this type of speciality, were studied over a period of 24 months.

| Product | $t_0$ | $t_6$ | $t_{12}$ | $t_{24}$ |
|---------|-------|-------|----------|----------|
| Composition A | 100.5 | 99.6 | 100.2 | 98.9 |
| Amoxicillin ($3H_2O$) | 100.0 | 99.2 | 99.6 | 98.5 |
| Composition A' | 99.8 | 98.8 | 97.8 | 93.7 |
| Amoxicillin Na | 100.0 | 97.3 | 94.8 | 90.2 |

Content of amoxicillin in % at time (in months)

The stability of the amoxicillin which is in the pulverulent state and which is included in composition A is comparable to that of the active material on its own, i.e. amoxicillin trihydrate, which is the reference.

By contrast, amoxicillin trihydrate which is combined solely with the solubilizer, i.e. sodium carbonate, exhibits instability beyond 12 months, with this instability appearing at 6 months in the case of sodium amoxicillin, which is the salified soluble form.

EXAMPLE 2

Soluble Composition Containing 50% Amoxicillin

In a similar manner to Example 1, amoxicillin (in trihydrate form) (50 g, that is 137 mmol) is mixed mechanically with anhydrous sodium carbonate (15 g, that is 141.5 mmol), monosodium phosphate dihydrate (5 g), sodium hexametaphosphate (20 g) and anhydrous glucose (10 g).

The same quantities of amoxicillin, that is. 10 g of the above-described composition, equivalent to 5 g of amoxicillin (in trihydrate form), and 5 g of amoxicillin (in sodium form) were separately dissolved in 1000 ml of tap water of 360 hardness; the time for dissolution and the pH of each of the solutions obtained were noted.

| Product | Time for dissolution | Final pH |
|---|---|---|
| Composition (10 g) | 46 sec | 7.75 |
| Amoxicillin (Na) (5 g) | 1 min 15 sec Residue of insoluble material | 8.8 |

The hardness of the water retards the solubilization of the active ingredient by leading to the formation of the insoluble calcium salt of the antibiotic. The composition which is produced in accordance with the present invention solubilizes the antibiotic while disregarding the quality of the water employed.

EXAMPLE 3

Soluble Composition Containing 20% Sulfamethazine

In a similar manner to Example 1, sulfamethazine (20 g) that is 71.85 mmol) is mixed mechanically with anhydrous sodium carbonate (8 g, that is 75.47 mmol), sodium chloride (18 g), trisaminomethane (5 g), an anti-caking agent (1 g) and anhydrous glucose (48 g).

This sulfamide is given to control infections due to Gram-positive organisms (Staphylococcus, Listeria, etc.) and Gram-negative organisms (*E. coli*, Klebsiella, Enterobacter, Proteus, Salmonella, etc.), and to control coccidia in calves, lambs, kids, pigs, rabbits and poultry. The posology is from 1.3 g to 1.7 g of sulfamethazine, that is from 6.5 to 8.5 g of composition/liter of drinking water for rabbits and poultry.

EXAMPLE 4

Soluble Paediatric Composition Containing 30% Cefalexin (in Monohydrate Form)

In a similar manner to Example 1, cefalexin (in monohydrate form) (30 g, that is 86.4 mmol) is mechanically mixed with anhydrous sodium carbonate (11 g, that is 103.77 mmol), citric acid (7 g), aspartame (0.5 g), an anti-caking agent (1 g), an aromatic composition (5 g) and disodiumphosphate (41.5 g).

The composition is aliquoted into 120 ml graduated glass bottles at the rate of 10 g per bottle, that is 3 g of cefalexin (in monohydrate form). The homogeneous solution of cefalexin is reconstituted by adding water in sufficient quantity to obtain 120 ml. This solution can be stored for several days. It is given to children at the rate of from 1 to 2 ml/kg/day, preferably in 2 or 3 doses during the course of the day.

As is evident from the above, the invention is in no way limited to those of its embodiments which have been described in more explicit manner; on the contrary, it encompasses all the variants of these embodiments of which the skilled person can conceive without departing from the context or the scope of the present invention.

We claim:

1. Pulverulent, water-soluble compositions, comprising, in combination and in pulverulent form:
   at least one non-salified active ingredient which is only soluble in water at alkaline pH,
   at least one salt of a strong base, which is present in excess, and
   at least one buffer, which is formed from one or more substances which are suitable for maintaining the pH of the medium at a value which is lower than the normal pH for solubilizing the said active ingredient.

2. A pulverulent composition according to claim 1, wherein the salt of the strong base is selected from the group consisting of basic salts which comprise, as anion, carbonate, bicarbonate or suphate ions and, as cation, sodium, potassium, ammonium or substituted ammonium ions.

3. A pulverulent composition according to claim 1 wherein the buffer is selected from the group which comprises phosphate buffers, leading to pH values of between 6.5 and 8.0, sodium chloride/disodium phosphate buffers, leading to pH values of between 6.8 and 7.5, sodium chloride/trisaminomethane buffers leading to a pH value of about 7.5, citro-phosphate buffers leading to pH values of between 6.5 and 7.9, and borate buffers leading to a pH value of about 7.5.

4. A pulverulent composition according to claim 1, wherein said composition additionally comprises at least one of the following compounds: chelating agents, anti-caking agents, flavours or perfumes or fillers, in the pulverulent state.

5. A pulverulent composition according to claim 1, wherein said composition contains between 1 and 60% (by weight based on the total pulverulent composition) of active ingredient.

6. Compositions in the form of aqueous solutions comprising a pulverulent composition according to claim 1 and water.

7. A process for preparing the said compositions in the form of aqueous solutions, comprising:
   (i) preparing a pulverulent composition comprising in combination and in pulverulent form:
      at least one non-salified active ingredient which is only soluble in water at alkaline pH,
      at least one salt of a strong base, which is present in excess, and
      at least one buffer, which is formed from one or more substances which are suitable for maintaining the pH of the medium at a value which is lower than the normal pH for solubilizing the said active ingredient; and
   (ii) solubilizing the said composition in a quantity of water which is sufficient for obtaining, in the final solution, a quantity of active ingredient per kg of animal to be treated which is effective for at least 24 hours.

8. A preparation process according to claim 7, wherein step (ii) can be carried out in two stages, namely preparation of a concentrated solution and dilution of the concentrated solution so as to obtain, in the final solution, a quantity of active ingredient per kg of animal to be treated which is effective for at least 24 hours.

9. A pharmaceutical composition for veterinary use to be administered orally, which comprises a composition according to claim 1 combined with at least one pharmaceutically acceptable excipient.

10. A pharmaceutical composition for human use to be administered orally, which comprises a composition according to claim 1 combined with at least one pharmaceutically acceptable excipient.

\* \* \* \* \*